United States Patent
Chang et al.

(10) Patent No.: US 7,278,327 B2
(45) Date of Patent: Oct. 9, 2007

(54) FILM BASED POSITION AND PRESSURE SENSOR

(75) Inventors: Timothy N. Chang, Montville, NJ (US); Biao Cheng, Edison, NJ (US)

(73) Assignee: New Jersey Institute of Technology, Newark, NJ (US)

( * ) Notice: Subject to any disclaimer, the term of this patent is extended or adjusted under 35 U.S.C. 154(b) by 115 days.

(21) Appl. No.: 11/189,338

(22) Filed: Jul. 26, 2005

(65) Prior Publication Data

US 2006/0016272 A1    Jan. 26, 2006

Related U.S. Application Data

(60) Provisional application No. 60/591,244, filed on Jul. 26, 2004.

(51) Int. Cl.
   *G01D 7/00* (2006.01)
   *F41A 17/20* (2006.01)

(52) U.S. Cl. ............ 73/862.041; 73/763; 42/70.06

(58) Field of Classification Search ........... 73/767, 73/818, 768, 769, 727, 763, 862.041; 42/70.06
   See application file for complete search history.

(56) References Cited

U.S. PATENT DOCUMENTS

| | | | | | |
|---|---|---|---|---|---|
| 4,456,013 | A | * | 6/1984 | De Rossi et al. | ............ 600/488 |
| 5,398,885 | A | * | 3/1995 | Andersson et al. | ......... 244/1 R |
| 5,840,036 | A | * | 11/1998 | Voith | ............... 600/493 |
| 6,131,464 | A | | 10/2000 | Pare, Jr. et al. | |
| 6,817,130 | B2 | * | 11/2004 | Ivanov | ............... 42/70.06 |
| 2002/0170220 | A1 | * | 11/2002 | Recce | ............... 42/70.08 |
| 2005/0034543 | A1 | * | 2/2005 | Xi et al. | ............. 73/862.634 |

OTHER PUBLICATIONS

Takanori et al., Pressure Sensor Chip, Tactile Sensor and Manufacture of Tactile Sensor, Jan. 20, 1995, Patent Abstracts of Japan, 07-019975.*

* cited by examiner

*Primary Examiner*—Michael Cygan
*Assistant Examiner*—Punam Patel
(74) *Attorney, Agent, or Firm*—Kaplan Gilman Gibson & Dernier LLP

(57) ABSTRACT

Simultaneous pressure and position information is accurately measured in a sensor realized by utilizing first and second sensor elements that each exhibit a decreasing width over the length of the sensor element and that are arranged overlapping each other and in a substantially complementary orientation to one another with respect to the width so that the point of narrowest width of the first sensor element overlaps the point of the widest width of the second sensor element. Pressure applied to the sensor causes each sensor element to generate an electrical signal that is proportional to both the applied pressure and the surface area at the location of the applied pressure. As a result of the complementary orientation and overlapping for these sensor elements, the first and second sensor elements generate an asymmetric pair of signals that uniquely define the applied pressure by position and magnitude.

28 Claims, 5 Drawing Sheets

FILM BASED POSITION AND PRESSURE SENSOR

CROSS-REFERENCE TO RELATED APPLICATIONS

This application claims the benefit of priority from U.S. Provisional Patent Application Ser. No. 60/591,244 filed on Jul. 26, 2004. The above-identified provisional patent application is incorporated by reference herein in its entirety.

GOVERNMENT RIGHTS

The United States government may have certain rights in this invention. A portion of the work described herein may have been supported in part by the National Institute of Justice under Grant 2004-IJ-CX-0096.

BACKGROUND OF THE INVENTION

1. Field of the Invention

This invention relates to sensor apparatus and, more particularly, to pressure and position sensing apparatus useful in robotics, biometric applications, and the like.

2. Description of the Related Art

Sensors activated by pressure have found a wide variety of applications in every day living, typically, in the form of thin touch pads. Microwave ovens have touch pads for programming cooking times, cellular telephones utilize touch pads as the key pads for dialing phone numbers, elevators have touch pads for calling an up or down elevator and for selecting a floor at which to stop, automated teller machines and computers have utilized touch screens for data entry and selection, intelligent robotic manipulators with pressure sensitive skins, and electronic lock systems such as those used in automobiles and the like use touch pads for keying in the electronic unlocking combination.

In general, these devices are binary devices and only require pressure to be applied at a predetermined position to produce an output. For example, when pressure is applied anywhere on the pad corresponding to the up arrow for an elevator, an up elevator will be called. The same is true for keying in a lock combination. In most cases, each discrete area of the pressure touch pad is individually wired to produce the sensed pressure output for that discrete area. That is, pressing the number "4" on a keypad anywhere on that keypad will produce a signal from the pressed sensor indicating that the number "4" has been pressed.

For the systems described above and other such similar systems, the occurrence of pressure being applied to the sensor is generally the only data that is gathered. The amount of pressure, that is the applied force, is not captured and, for these systems, is usually meaningless. For example, it is only meaningful that a person presses the pad for a down elevator; it is not usually meaningful that the pad is pushed lightly or very hard. Hence, these systems operate in a digital binary mode (e.g., pressure/no pressure) rather than an analog mode (e.g., a continuum of no pressure through heavy pressure).

Position information is not captured by most of these systems. If a person presses an up elevator pad anywhere on the face of the pad, the result is the same and an ascending elevator is called. On a microwave oven, the touch pad is demarcated so that each discrete area corresponds to a particular function (e.g., defrosting or heating popcorn) or a particular number. Pressure on the touch pad between a "1" and a "2" generally produces either one of the two numbers or no response at all and it certainly does not produce an analog result (i.e., a real number) between 1 and 2 based on the point of pressure.

In some applications, a limited amount of predefined position information can be made available. The limited position information is made available by row and column grid arrangements in certain touch screens that indicate the relative position of applied pressure. The position location is relative because it can be accurately located only to the closest grid intersection of a row and a column. In these grid arrangements, it is impossible to measure or resolve the actual position of an applied force when the force is not applied directly over a particular row and column intersection.

Although various devices and systems have been proposed for pressure sensing, none have presented a practical solution that can be employed for simultaneous measurement of the amount of applied pressure and the actual position over a continuous range of positions.

SUMMARY OF THE INVENTION

Simultaneous pressure and position information is accurately measured by a sensor realized in accordance with the principles of the present invention by utilizing first and second sensor elements that each exhibit a decreasing width over the length of the sensor element and that are arranged overlapping each other and in a substantially complementary orientation to one another with respect to the width so that the point of narrowest width of the first sensor element overlaps the point of the widest width of the second sensor element. Pressure applied to the sensor causes each sensor element to generate an electrical signal that is proportional to both the applied pressure and the surface area at the location of the applied pressure. As a result of the complementary orientation and overlapping for these sensor elements, the first and second sensor elements generate an asymmetric pair of signals that uniquely define the applied pressure by position and magnitude.

In one embodiment, a 1-dimensional sensor is realized by first and second sensor elements that are substantially linear. The elements are arranged in the complementary orientation with a substantial overlapping of their respective longitudinal axes. For this embodiment, position information is limited to a continuum of points along the longitudinal axis of the sensor.

In another embodiment, a 2-dimensional sensor is realized by first and second sensor elements whose major axis (i.e., the axis that is substantially normal to the transverse axis exhibiting the variation in width) includes a set of mutually exclusive points defining a plane. Exemplary shapes for the sensor elements in this embodiment are a spiral, a spiral-like shape that exhibits substantially polygonal features as opposed to circular features, a zigzag or serpentine shape, a folded serpentine or raster scan shape, and the like. The elements are arranged in the substantially complementary orientation with a substantial overlapping of their respective major axes. Position information is again limited to a continuum of points along the major axis of the sensor, which map to (x,y) coordinates because of the 2-dimensional configuration for this embodiment.

In another embodiment, 3D sensing can be achieved by applying the 1D or 2D sensor element onto a surface such as a curved or irregular surface.

The sensor elements can be realized using most film and non-film materials. Piezoelectric and piezoresistive materials are useful in realizing the sensor elements. Other modalities include capacitive and electrostatic films. Flexible materials such as polymer films allow the sensors to be more easily adapted to a wide variety of flat and curved surfaces.

Processing circuitry such as electrical amplifiers, signal processors, table lookup memory, and the like is used to couple the generated signals from each sensor element and then to translate the information in each signal pair into a corresponding position and magnitude for the applied pressure.

A sensor realized in accordance with the principles of the present invention offers the ability to measure the actual position and magnitude of an applied force over a substantially continuous range using a minimal number of electrical interconnections. When flexible film materials are used for the sensor, it is possible to conform the sensor to a wide range of surface configurations. One exemplary use of such a sensor is in the area of biometrics as applied to "smart gun" technology for obtaining the applied force and size of the user's hand when gripping a firearm.

BRIEF DESCRIPTION OF THE DRAWINGS

A more complete understanding of the invention may be obtained by reading the following description of specific illustrative embodiments of the invention in conjunction with the appended drawings in which.

Figure 1:
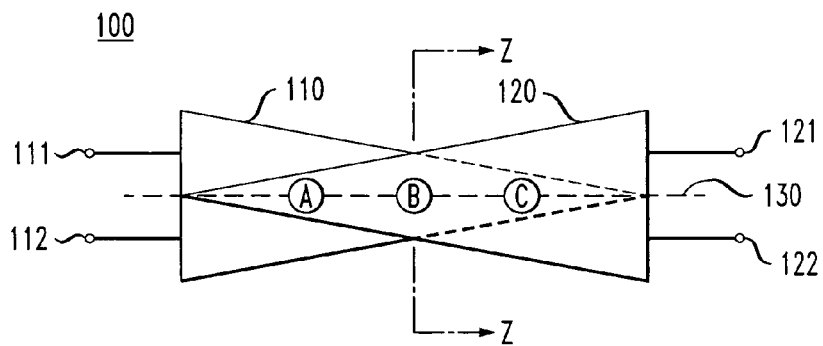
FIG. 1 shows a simplified diagram of a sensor realized in accordance with the principles of the present invention.

It should be noted that the appended drawings illustrate only typical embodiments of this invention that are not necessarily drawn to scale and are therefore not to be construed as limiting of its scope. The practice of the present invention may admit to other equally effective embodiments in addition to those shown in the drawings. It should be noted that the embodiments in the figures are not necessarily drawn to scale. Where possible, identical reference numerals have been inserted in the figures to denote identical elements.

DETAILED DESCRIPTION

In the description that follows, certain terms are used interchangeably. The terms "sensing element" and "sensor element" define the component elements of the sensor and are use interchangeably. These usages are not intended to be limiting in any way.

FIG. 1 shows an exemplary sensor 100 realized in accordance with the principles of the present invention for accurate and simultaneous measurement of pressure and position for an applied force. Sensor 100 includes first and second sensor elements 110 and 120 that each exhibit a tapered or decreasing width over the length of the sensor element and that are arranged to be both overlapping each other and in a substantially complementary orientation to one another with respect to the width so that the point of narrowest width of the first sensor element overlaps the point of the widest width of the second sensor element.

In FIG. 1, a 1-dimensional sensor is realized by first and second sensor elements 110 and 120. These sensor elements are substantially linear with tapered sides. Each element has a longitudinal axis 130 substantially normal to the width of each element. The elements are arranged in the complementary orientation with a substantial overlapping of their respective longitudinal axes so that the narrowest portion of element 120 overlaps the widest portion of element 110 and vice versa. It is desirable to have the overlapped sensor elements being coextensive lengthwise.

Pressure applied to the sensor causes each sensor element 110 and 120 to generate an electrical signal that is proportional to both the applied pressure and the surface area at the location of the applied pressure. As a result of the complementary orientation and overlapping for these sensor elements, first and second sensor elements 110 and 120 generate an asymmetric pair of signals that uniquely define the applied pressure by position and magnitude. The signals are output from leads 111 and 112 for the first sensor element and from leads 121 and 122 for the second sensor element. In this embodiment, position and pressure information is available for the continuum of points along longitudinal axis 130 of sensor 100. For example, pressure applied at any location along or around longitudinal axis 130 such as those positions labeled A, B and C in FIG. 1 can be accurately measured and located.

Figure 3:
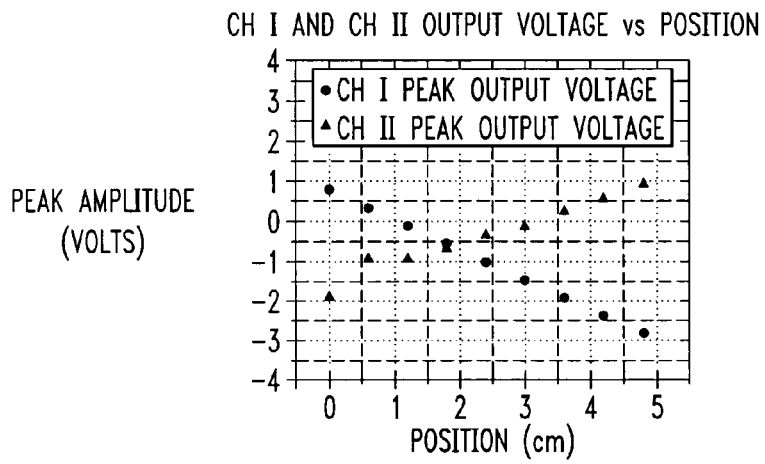
FIG. 3 shows a plot of peak output amplitude versus position for the exemplary sensor in FIG. 1.

The asymmetry attributed to pair of sensor output signals described above can be more easily understood by observing the response to pressure applied at designated locations A, B, and C in FIG. 1. Pressure applied via the sensor to each sensor element generates signals whose magnitudes are proportional to the cross-sectional areas of the respective overlapping sensor elements at the point of the applied force. Since sensor element 120 is quite narrow in comparison to the overlapped width of sensor element 110 at location A, the signal output by sensor element 120 is proportionally smaller than the signal output by sensor 110 for the same applied force. Since sensor element 120 is substantially the same width as overlapped sensor element 110 at location B, the signals output by sensor elements 120 and 110 are substantially equal for the same applied force. Since sensor element 120 is significantly wider at location C than overlapped sensor element 110, the signal output by sensor element 120 is proportionally larger than the signal output by sensor 110 for the same applied force. When the sensor output signal response is viewed graphically as a voltage signal for a constant pressure as shown in FIG. 3 for an exemplary piezoelectric sensor from experimental practice, the sensor output from first sensor element 110 decreases from a high value to a much lower value for pressure applied from left to right across the entire sensor whereas the sensor output from second sensor element 120 increases from a low value to a much higher value for pressure applied from left to right across the entire sensor. This asymmetric signal response, as shown in the pair of curves in FIG. 3, permits the position of the applied pressure to be calibrated and determined uniquely with complete accuracy. Similarly, the pair of signal values also allows for an accurate determination of the applied pressure.

Figure 2:
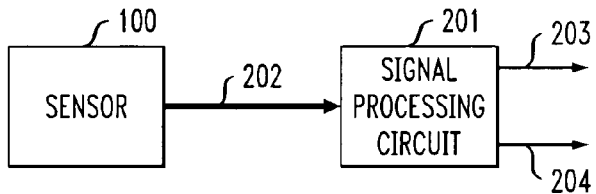
FIG. 2 shows a diagram of the sensing system including the sensor in FIG. 1.

FIG. 2 shows the sensing system in which sensor 100 is coupled to signal processing circuit 201. When a pressure is applied to sensor 100, the output signals are supplied on lead or leads 202 to signal processing circuit 201. Circuit 201 processes the supplied signals to determine the position at which the pressure is applied and the amount of pressure applied. In this exemplary system, position is output via lead 203 while the pressure magnitude is output via lead 204. It is contemplated that, in certain applications, it may be desirable to determine either the position of the applied pressure or the amount of the applied pressure instead of both quantities. For arrays of such sensors, it is then possible to obtain individual measurements from each one of the plurality of sensors so that, for example, mapping of the characteristics of hand pressure on a firearm grip can be accomplished.

Processing circuitry is used to couple the generated signals from each sensor element and then to translate the information in each signal pair into a corresponding position and magnitude for the applied pressure. Signal processing circuit 201 generally includes pre-amplifiers coupled to the sensor output leads in order to condition and amplify the sensor output signals prior to further processing. In one example from experimental practice, the processing circuit includes analog-to-digital converters for digitizing the output signals from the signal processing circuit 201, and a computer based table lookup element responsive to both digitized output signals for recalling the stored position and pressure information from the storage table in the lookup element. Alternative measurements can be made using other signal processing circuits such as an ASIC or digital signal processor (DSP) that is calibrated to the particular sensor and that responds to the sensor output signals to calculate the precise position and pressure. Since these types of circuits are well known in the art and commercially available, they will not be disclosed in further detail.

In an example from experimental practice, a sensor utilizing triangular sensor elements as depicted in FIG. 1 was realized using polyvinylidene fluoride (PVDF) polymer film for each sensor element. The area of complementary overlap for the sensor elements was approximately 4.8 cm. A constant pressure was applied at distinct locations in the overlap area to produce sensor element output signal amplitudes as plotted by the curves in FIG. 3. The decreasing output voltage (signal viewed from left to right) labeled as Channel I, which is plotted using circles, appears at the sensor element 110 output on leads 111 and 112; and the increasing output voltage (signal viewed from left to right) labeled as Channel II, which is plotted using triangles, appears at the sensor element 120 output on leads 121 and 122. Design imperfections caused crossover point of the curves to occur at other than the midpoint of the overlap area, that is, at approximately 1.9 cm rather than 2.4 cm.

As described above, the present sensor structure represents a reduction in output ports by requiring only two output ports to provide a 1-dimensional output whereas a corresponding grid or dot-matrix structure would require N+1 output ports (one row output port and N column output ports). Moreover, the present inventive structure has effectively infinite resolution by providing a distinct output for each possible position continuously along the main axis of the sensor—that is, an infinite number of applied pressure positions—while a grid structure only allows for a discrete, finite resolution into N possible positions along the sensor axis.

Figure 7:
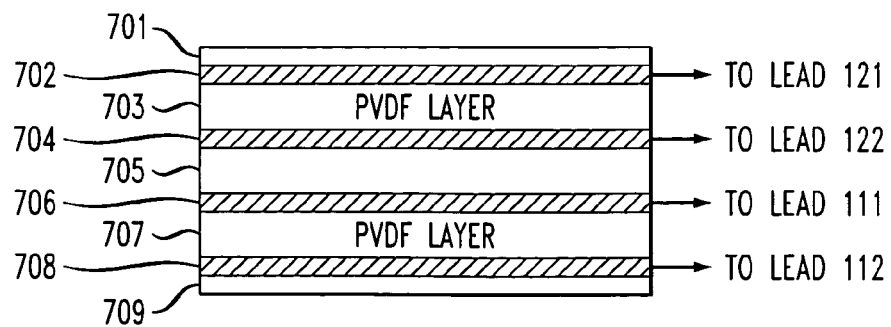
FIG. 7 shows a portion of the cross-sectional multiplayer structure for the sensor in FIG. 1 taken through the section line Z-Z.

In the preferred embodiment shown in FIG. 1, the sensor elements are realized by forming commercially packaged PVDF films into the desired shape and by overlapping the two sensor elements by the desired amount. Commercially available PVDF films are prepackaged in a sealed rectangular strip form with upper and lower metallic (silver) electrode layers surrounding the PVDF film, metallic contacts attached to the electrode layers, pigtail wires attached to the contacts, and a urethane jacket encapsulating the entire structure. The films can be directly fabricated into the desired shape or they can be cut from commercially available rectangular strips. An etchant such as 50% nitric acid is applied to the packaged film to dissolve any metallization on the edges thereby preventing short circuiting of the top and bottom conductive layers and producing the desired triangular shape. Care is taken to insure that the electrodes avoid shorting with one another. When patterning is complete, the newly shaped sensor elements are overlapped and attached together using epoxy such as standard 5-minute epoxy to form the sensor. The pigtail wires are attached to the processing circuit and the sensor is calibrated. An exemplary layer structure is shown in FIG. 7 and will be described in more detail below.

Although PVDF films have been used for the embodiments described herein, it is contemplated that other materials will provide desirable characteristics for realizing the present invention. Flexible sensor structures can be realized from PVDF film and other piezoelectric compounds such as lead zirconate and lead titanate (PZT), for example which may be coated onto a conductive substrate. More rigid sensor structures can be realized by using piezoelectric ceramic wafers. Piezoresistive compounds can also be used in place of the piezoelectric ones such as monocrystalline silicon. It should be understood by persons skilled in the art that the present sensor can be realized by any compound that provides an output signal in response to an applied pressure.

Rigidity of the sensor is an important characteristic that determines the suitability of the sensor for certain applications. Flexible materials such as polymer films allow the sensors to be more easily adapted to a wide variety of flat and curved surfaces. It may be necessary to have a highly flexible sensor that is to be placed over and conformed to an irregular or regular curved surface for a particular application. One such application could be in the so-called "smart gun" technology where biometric measurements are taken from the user before unlocking the safety mechanism for the gun or other firearm. These biometric measurements could involve the size and pressure profile of the user's hand. A flexible realization of the present sensor is well suited to take these biometric measurements. Other such uses are contemplated for either flexible or more rigid adaptations of the sensor.

Figure 4:
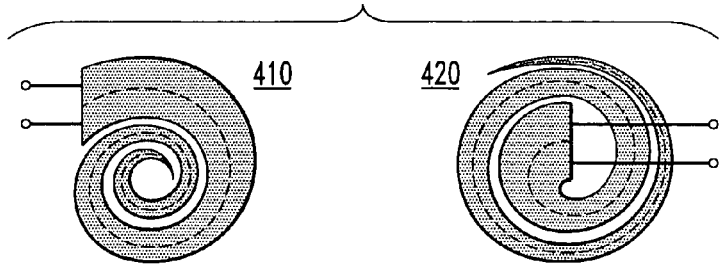
FIG. 4 shows an exemplary sensor element pattern for a 2-dimensional sensor using a spiral shaped sensor element.
Figure 5:
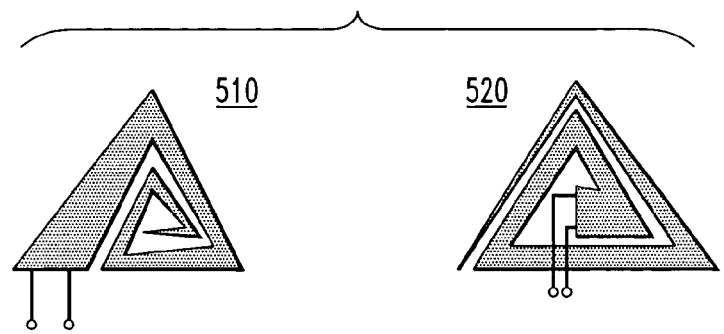
FIG. 5 shows an exemplary sensor element pattern for an alternative 2-dimensional sensor using a spiral-like polygonal shaped sensor element.
Figure 6:
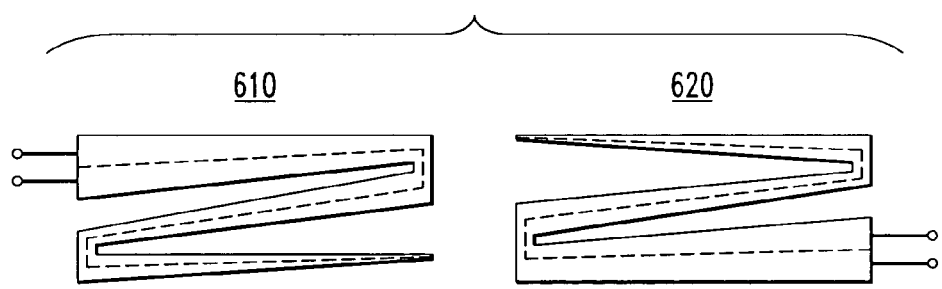
FIG. 6 shows an exemplary sensor element pattern for an alternative 2-dimensional sensor using a serpentine or zigzag shaped sensor element.

A 2-dimensional sensor is realized by first and second sensor elements that meander over a nonlinear set of points defining a plane. Simply put, each sensor element includes a major axis, which is substantially normal to the transverse axis or width of the element. The major axis of the sensor element traverses a set of mutually exclusive points in a plane thereby causing the sensor element to be at least capable of providing 2-dimensional readings. Exemplary shapes for the 2-dimensional sensor elements in this embodiment are a spiral as shown in FIG. 4, a spiral-like shape that exhibits substantially polygonal features as opposed to circular features as shown in FIG. 5, a serpentine or zigzag shape as shown in FIG. 6, a folded serpentine or raster scan shape. This presentation of sensor element shapes in the figures is not intended to be limiting in any way. It is expected that, based on the particular application, many other shapes can be realized without departing from the spirit and scope of the invention. Certain shapes will permit a closer packing of the sensors within a specific area thereby allowing greater sensor coverage and accuracy over the desired area. For example, a spiral-like shape following a polygon such as a hexagon could allow for very efficient and substantially complete coverage of an area by using hexagonal close packing of the sensors.

In order to realize the sensor, the sensor elements are arranged in the substantially complementary orientation as taught with respect to the embodiment in FIG. 1 with a substantial overlapping of their respective major axes. For the sensor elements shown in FIGS. 4-6, the overlap can be developed by sliding the element on the right directly over or under the element on the left without any rotation of the elements. In this way, there is overlap with the complementary orientation and the asymmetry of the output signal is preserved. For example, the spiral element 410 can be placed over the spiral element 420 with major axes (dashed lines not shown to scale) overlapping. Similarly, polygonal (triangular) spiral-like element 510 can be placed over the polygonal (triangular) spiral-like element 520 with major axes (dashed lines not shown to scale) overlapping. Finally, serpentine or zigzag element 610 can be placed over the serpentine or zigzag element 620 with major axes (dashed lines not shown to scale) overlapping.

Operation of the 2-dimensional sensors is similar to that of the 1-dimensional sensor. Position information is again obtained for a continuum of points along the major axis of the sensor. But, as the sensor is traversed along the major axis (shown as a dashed line in the figures), each point maps to an (x,y) coordinate in a plane because the embodiment is in a 2-dimensional configuration.

The 2-dimensional sensors shown in FIGS. 4-6 provide position and pressure information via their output signals via only 2 output ports. The sensor is designed to provide significant coverage over a particular planar area with substantially infinite resolution of the position of applied pressure in the 2D space. In contrast, coverage of the same area by a grid or dot matrix structure requires N-row outputs and M-column outputs and provides only finite discrete coverage of the area limited to only N×M positions.

Figure 10:
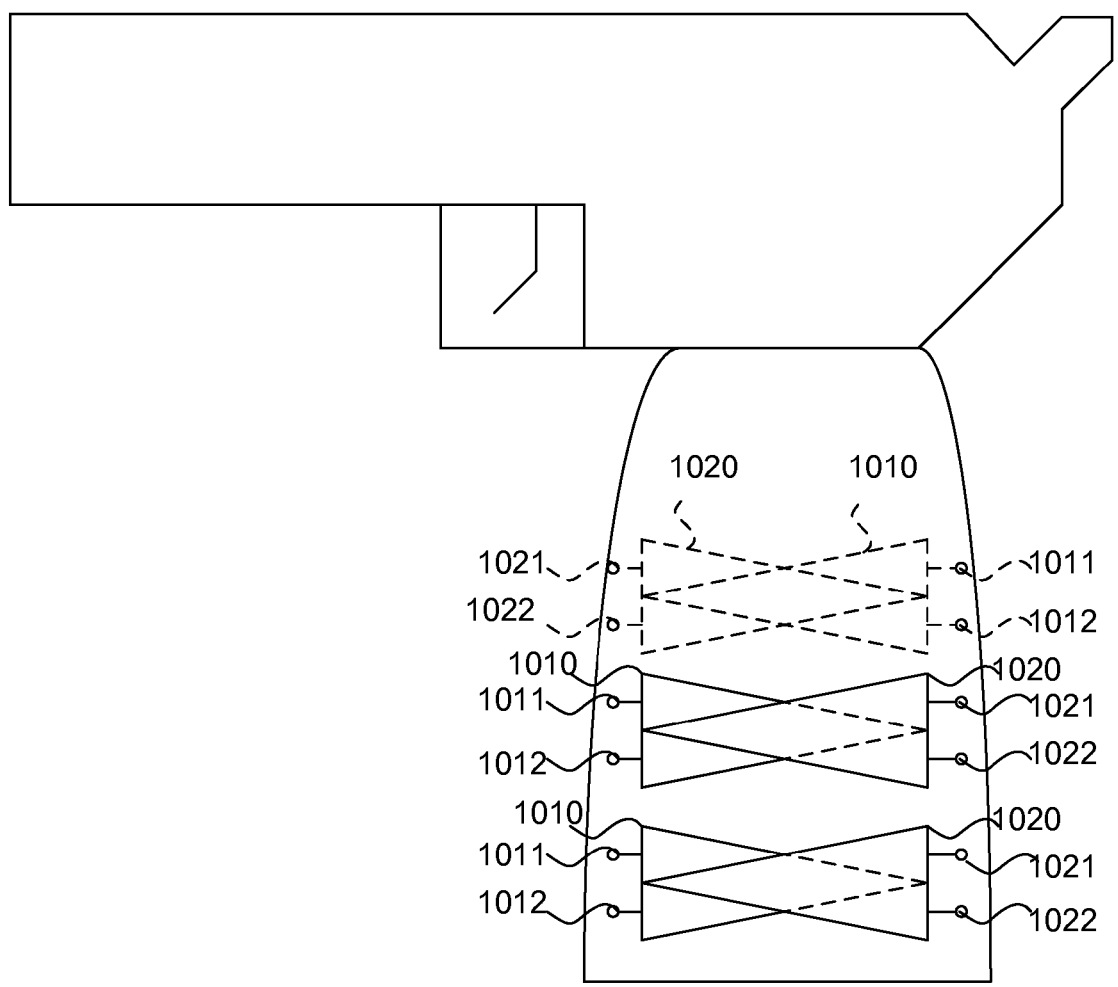
FIG. 10 shows an alternative design of the exemplary 1D sensor elements disposed on a predetermined surface area of a gun handle.

A 3D embodiment of the present invention is realized by wrapping flexible 1D or 2D elements onto a surface such as a firearm grip for a "smart" gun application. In FIG. 10, the gun handle has 1-dimensional sensor elements from FIG. 1 disposed on its predetermined surface area for such a "smart" gun application. The sensor then takes on the dimensionality of the underlying surface to which it conforms. It is contemplated that these grips can be realized with embedded sensors thereby permitting the use of less flexible materials for the sensors in addition to flexible materials.

It will be apparent to persons skilled in the art that each sensor element pattern exhibits an increasing or decreasing width as the element is traversed from one end to the opposite end. This tapering of the width can be realized as a linear taper or a curved taper or another type of nonlinear taper such as a quadratic taper. The degree or slope of the taper can have an effect on the accuracy of the measurements of applied pressure position and magnitude. If the taper is very gradual, it is possible that the observable differences in sensor output signals for adjacent positions can be insignificant, whereas, if the taper is more steep, the observable differences in sensor output signals for adjacent positions will be more significant.

Figure 9:
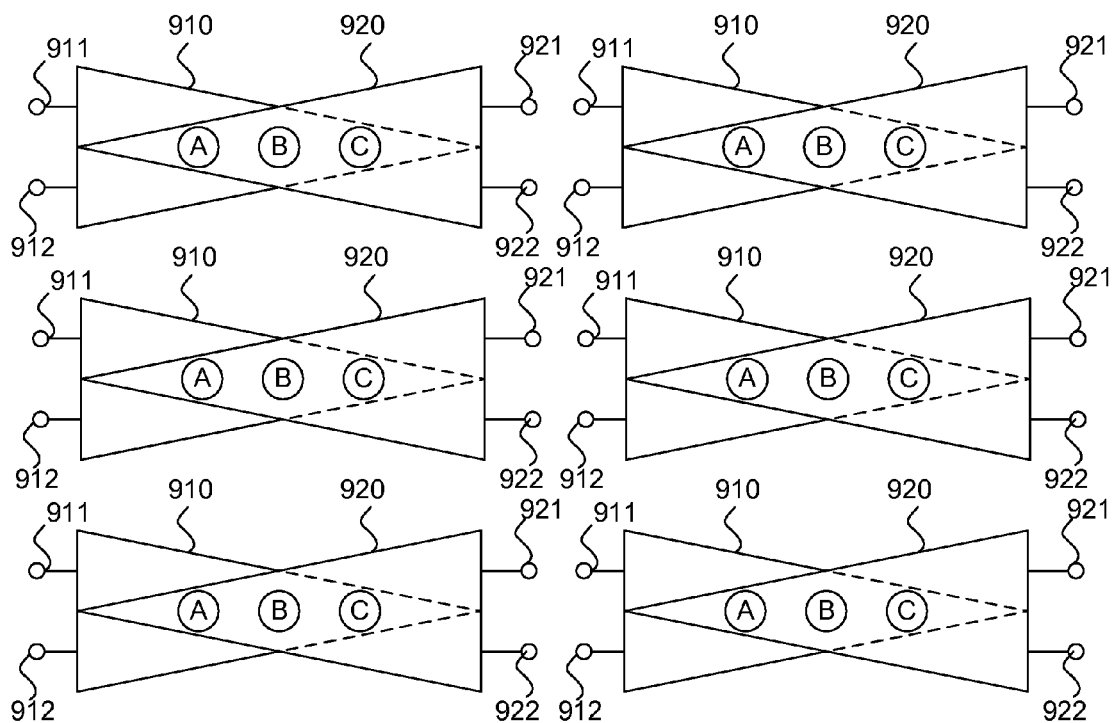
FIG. 9 shows an alternative design of the exemplary sensor using sensor elements arranged side-by-side in a series of rows or columns to cover a larger surface area than a single sensor.

It is contemplated that a plurality of sensors can be arranged in arrays to cover a larger area. For example, a plurality of the exemplary linear 1-dimensional sensors shown in FIG. 1 can be arranged side-by-side in a series of rows or columns to cover a much larger area as shown in FIG. 9. Each of the sensors can be coupled to a corresponding one of a plurality of signal processing circuits. Alternatively, the plurality of sensors in the array could be coupled to a single signal processing circuit that is programmed to differentiate among the sensor outputs in order to provide the corresponding applied pressure magnitude and position information. Similarly to the array of 1-dimensional sensors, the 2-dimensional patterns can also be arrayed to cover a much larger area.

The sensor elements can be fabricated by standard methods to create a multilayer structure as shown for the exemplary embodiment in FIG. 7. FIG. 7 is a cross-sectional view seen through cut line Z-Z for the multilayer structure of the sensor shown in FIG. 1. The multilayer structure includes pressure sensitive PVDF layers 703 and 707, electrode layers 702, 704, 706, and 708, and compliant insulator layers 701, 705, and 709. Electrode layers conduct the responsive electrical charge signal to respective contacts and output leads (not shown). Thin metallic layers such as a deposited silver layer can be utilized for the electrode layers. Compliant insulator layers maintain electrical isolation between the overlapping sensor elements as well as providing protection from the ambient environment. Urethane or a compliant oxide can be deposited for the insulation layers. The entire structure in FIG. 7 can be formed on a substrate or attached to a surface of a particular object based on the desired application for the sensor.

Throughout the description above, it has been assumed for ease of disclosure that the sensor elements for the 1-dimensional sensor have identical or substantially identical shapes. But it is also contemplated that the first sensor element and the second sensor element have different shapes or tapers provided that the complementary overlap can still be adequately achieved to realize the desired results. Such an embodiment is shown in FIG. 8.

Figure 8:
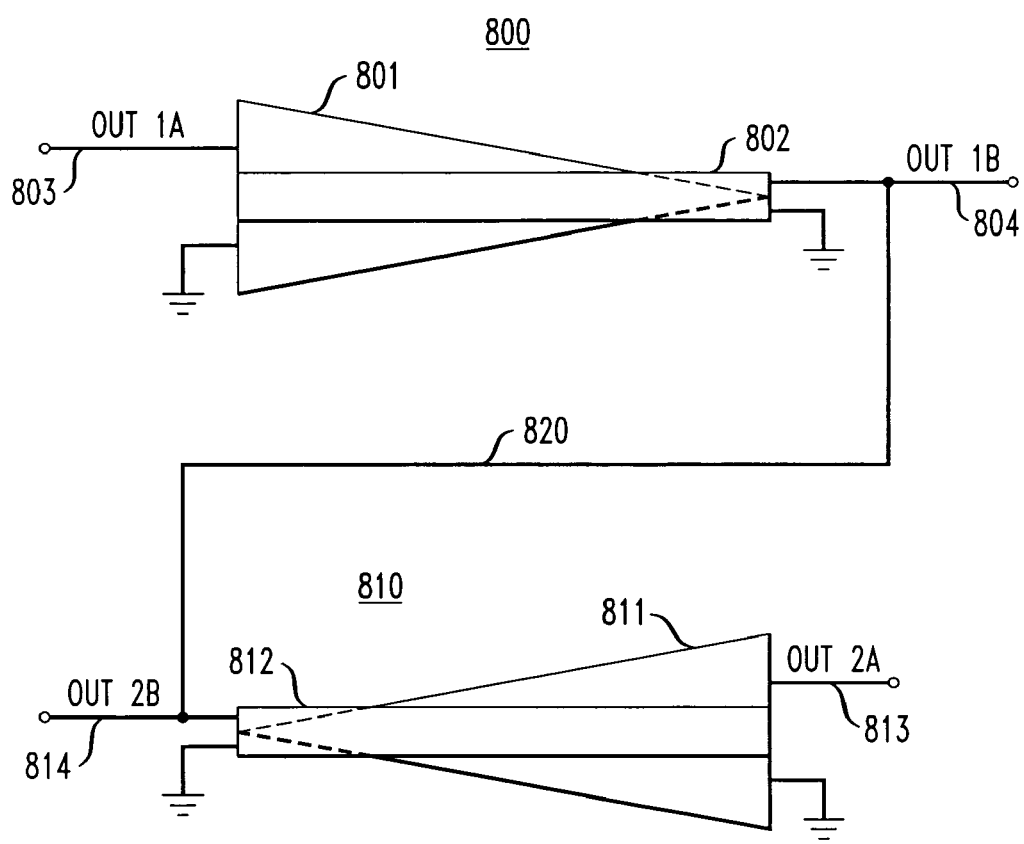
FIG. 8 shows an alternative design of the exemplary sensor using sensor elements having different shapes.

In FIG. 8, sensors 800 and 810 are shown wherein the individual sensor elements in each sensor have different shapes. The sensors 800 and 810 are interconnected to demonstrate the formation of a two sensor 2-dimensional array having a minimum number of output leads.

For the exemplary embodiment shown in FIG. 8, each sensor includes a sensor element having one shape and another sensor element having a different shape. Particularly, in sensor 800, sensor element 801 is shaped as a triangle and sensor element 802 is substantially rectangular and, in sensor 810, sensor element 811 is shaped as a triangle and sensor element 812 is substantially rectangular. The sensor elements in each sensor overlap along their main axes. In the interconnected configuration, the triangular sensor elements 801 and 811 are arranged in a complementary orientation. Output signals from sensor 800 are supplied on leads 803 (signal OUT1A) and 804 (OUT1B) whereas output signals from sensor 810 are supplied on leads 813 (signal OUT2A) and 814 (OUT2B). Separate leads are used as ground connections for each sensor element output. Lead 820 interconnects the two sensors between lead 804 and 814. Outputs OUT1B and OUT2B are the same and only one lead is needed for connection to the signal processing circuitry.

As a result, this embodiment uses only N+1 (N=2 tapered elements) outputs to obtain an accurate measure of position and amount for an applied force.

It is contemplated that integrated and hybrid designs can be utilized for the sensor and sensor system. In an integrated solution, the sensor system would include the sensor or sensors (for an array) and processing circuitry in the same package.

In the raster design approach, it is also contemplated that a very thin strip can be used on the flyback or retrace path so that only the left-to-right paths are tapered and the right-to-left paths are very thin and not tapered.

Although a fully tapered shape has been shown in the figures, it should be understood by persons skilled in the art that the narrow end of the taper can be a measurable width other than a point. In this way, the sensor elements in FIG. 1 could be realized as trapezoids instead of triangles.

While the foregoing is directed to embodiments of the present invention, other and further embodiments of the invention may be devised without departing from the basic scope thereof, and the scope thereof is determined by the claims that follow. For example, it is contemplated that other sensor properties can be used in tapering to provide the signal differences with changing position. It is contemplated that the thickness of one or both sensor elements can be tapered from one end to the other. Also the material composition of the sensor element such as the PVDF film or other material can be continuously graded in composition so that the output signal for each sensing element is different as the position of applied force changes along the major axis of the sensor element.

The invention claimed is:

1. Apparatus for sensing an applied pressure, the apparatus comprising:
first and second sensing elements wherein each of said first and second sensing elements generates an electrical signal in response to said applied pressure, wherein each of said first and second sensing elements exhibits a width that tapers with increasing distance along a major axis of each sensing element, wherein the first sensing element and the second sensing element are in a substantially parallel orientation with at least some area of complementary overlapping, and wherein the first sensing element is disposed in a complementary orientation to the second sensing element with respect to the width.

2. The apparatus as defined in claim 1 wherein the first sensing element is substantially similar in shape and length along the major axis to the second sensing element.

3. The apparatus as defined in claim 2 wherein said taper is substantially linear and monotonically decreasing.

4. The apparatus as defined in claim 2 wherein said taper is substantially nonlinear and monotonically decreasing.

5. The apparatus as defined in claim 2 wherein at least the first sensing element comprises substantially flexible pressure sensing material.

6. The apparatus as defined in claim 5 wherein the substantially flexible pressure sensing material is a polyvinylidene fluoride (PVDF) polymer film.

7. The apparatus as defined in claim 5 wherein the at least first sensing element includes a substantially flexible multilayer pressure sensing structure having a PVDF layer between top and bottom contact layers for conducting the electrical signal generated in response to the applied pressure.

8. The apparatus as defined in claim 1 wherein at least the first sensing element exhibits a substantially triangular shape.

9. The apparatus as defined in claim 8 wherein the second sensing element exhibits a substantially triangular shape and the major axis for each of the first and second sensing elements prescribes a substantially serpentine shape.

10. The apparatus as defined in claim 8 wherein the second sensing element exhibits a substantially triangular shape and the major axis for each of the first and second sensing elements prescribes a substantially spiral shape so that each sensing element covers a substantially circular area.

11. The apparatus as defined in claim 8 wherein the second sensing element exhibits a substantially rectangular shape.

12. The apparatus as defined in claim 1 wherein at least the first sensing element exhibits a substantially trapezoidal shape.

13. The apparatus as defined in claim 1 wherein the major axis for each of the first and second sensing elements prescribes a substantially spiral shape and the first and second sensing elements each exhibit a shape that causes each sensing element to cover a substantially similar polygonal area.

14. The apparatus as defined in claim 13 wherein the substantially similar polygonal area is triangular.

15. The apparatus as defined in claim 13 wherein the substantially similar polygonal area is hexagonal.

16. The apparatus as defined in claim 1 wherein the first and second sensing elements include pressure sensing materials selected from the group of materials including piezoresistive material and piezoelectric material.

17. The apparatus as defined in claim 16 wherein the pressure sensing material is sufficiently flexible to permit the apparatus to be applied to and conform to a surface.

18. The apparatus as defined in claim 1 further including a signal processing circuit coupled to the first and second sensing elements and responsive to said signals from the first and second sensing elements to determine at least a position of the applied pressure on the apparatus.

19. The apparatus as defined in claim 1 further including a signal processing circuit coupled to the first and second sensing elements and responsive to said signals from the first and second sensing elements to determine at least an amount of the applied pressure on the apparatus.

20. Apparatus for sensing an applied pressure, the apparatus comprising:
a plurality of paired first and second sensing elements wherein each of said first and second sensing elements generates an electrical signal in response to said applied pressure, wherein each of said first and second sensing elements exhibits a width that tapers with increasing distance along a major axis of each sensing element, wherein the first sensing element and the second sensing element are arranged in a substantially parallel orientation with at least some area of complementary overlapping, and wherein the first sensing element is disposed in a complementary orientation to the second sensing element with respect to the width, and wherein the plurality of paired first and second sensing elements is arranged in an array to cover a predetermined surface area.

21. The apparatus as defined in claim 20 wherein the plurality of paired first and second sensing elements exhibits a shape that causes each sensing element to cover a substantially similar polygonal area and the array is close-packed.

22. The apparatus as defined in claim 20 further including a signal processing circuit coupled to the plurality of paired first and second sensing elements and responsive to said signals to determine at least a position of the applied pressure on the apparatus at each paired first and second sensing element.

23. The apparatus as defined in claim 20 further including a signal processing circuit coupled to the plurality of paired first and second sensing elements and responsive to said signals to determine at least an amount of the applied pressure on the apparatus at each paired first and second sensing element.

24. The apparatus as defined in claim 20 wherein the predetermined surface area is a portion of a firearm.

25. Apparatus for sensing an applied pressure, the apparatus comprising:

first and second sensing elements wherein each of said first and second sensing elements generates an electrical signal in response to said applied pressure, wherein each of said first and second sensing elements exhibits a predetermined characteristic that decreases with increasing distance along a major axis of each sensing element, wherein the first sensing element and the second sensing element are arranged in a substantially parallel orientation with at least some area of complementary overlapping, and wherein the first sensing element is disposed in a complementary orientation to the second sensing element with respect to the predetermined characteristic.

26. The apparatus as defined in claim 25 wherein the predetermined characteristic is selected from the group consisting of sensing element width, sensing element thickness, and sensing element material composition.

27. Apparatus for sensing an applied pressure, the apparatus comprising:

first and second sensing elements wherein each of said first and second sensing elements generates an electrical signal in response to said applied pressure, wherein each of said first and second sensing elements exhibits a predetermined characteristic that decreases with increasing distance along a major axis of each sensing element, wherein the first sensing element and the second sensing element are arranged in a substantially parallel orientation with at least a mutual point adapted to receive said applied pressure, and wherein the first sensing element is disposed in a complementary orientation to the second sensing element with respect to the predetermined characteristic.

28. The apparatus as defined in claim 27 wherein the predetermined characteristic is selected from the group consisting of sensing element width, sensing element thickness, and sensing element material composition.

* * * * *